(12) United States Patent
Wolff

(10) Patent No.: US 9,161,862 B2
(45) Date of Patent: Oct. 20, 2015

(54) ASSEMBLY FOR TAKING UP MENSTRUAL FLUID

(76) Inventor: Oded Wolff, Rotterdam (NL)

( * ) Notice: Subject to any disclaimer, the term of this patent is extended or adjusted under 35 U.S.C. 154(b) by 262 days.

(21) Appl. No.: 13/699,919

(22) PCT Filed: May 25, 2011

(86) PCT No.: PCT/NL2011/050360
§ 371 (c)(1),
(2), (4) Date: Feb. 5, 2013

(87) PCT Pub. No.: WO2011/149347
PCT Pub. Date: Dec. 1, 2011

(65) Prior Publication Data
US 2013/0131624 A1 May 23, 2013

(30) Foreign Application Priority Data

May 25, 2010 (NL) ...................................... 2004766

(51) Int. Cl.
*A61F 13/20* (2006.01)
*A61F 13/34* (2006.01)
*A61F 13/84* (2006.01)
*A61F 13/551* (2006.01)

(52) U.S. Cl.
CPC ............. *A61F 13/34* (2013.01); *A61F 13/2051* (2013.01); *A61F 2013/55195* (2013.01); *A61F 2013/8402* (2013.01)

(58) Field of Classification Search
CPC .. A61F 13/34; A61F 13/20; A61F 2013/8402
USPC .................... 604/385.17, 385.18, 904, 385.13
See application file for complete search history.

(56) References Cited

U.S. PATENT DOCUMENTS 3,674,029 A * 7/1972 Bates et al. .................... 604/366
5,891,123 A * 4/1999 Balzar ...................... 604/385.18
7,238,173 B1 * 7/2007 Dobbs ...................... 604/385.13

FOREIGN PATENT DOCUMENTS

DE 20 2009 009072 U1 12/2009
WO 03/015676 A2 3/2003

OTHER PUBLICATIONS

International Search Report under date of Aug. 31, 2011 in connection with PT/NL2011/050360.

* cited by examiner

*Primary Examiner* — Jacqueline Stephens
(74) *Attorney, Agent, or Firm* — Quarles & Brady LLP

(57) ABSTRACT

The invention relates to an assembly for taking up menstrual fluid. The assembly comprises a fluid absorbing module and a cord of which a first end is connected to the fluid absorbing module and of which a second end is free. The cord further comprises a string and a covering with an open and a closed end which, before use of the assembly, substantially surrounds the string. The closed end of the covering is fixed to the string adjacent the first end of the cord.

18 Claims, 2 Drawing Sheets

ASSEMBLY FOR TAKING UP MENSTRUAL FLUID

CROSS-REFERENCE TO RELATED APPLICATIONS

This application represents the national stage entry of PCT International Application No. PCT/NL2011/050360 filed on May 25, 2011 and claims the benefit of Netherlands Patent Application No. 2004766 filed May 25, 2010. The contents of both of these applications are hereby incorporated by reference as if set forth in their entirety herein.

The invention relates to an assembly for taking up menstrual fluid, comprising a fluid absorbing module and a cord, of which a first end is connected to the fluid absorbing module and of which a second end is free.

Such assemblies are known for taking up menstrual fluid. Known tampons usually have an elongate, fluid absorbing module and a cord for pulling the module from the vagina after use.

In practice, after use, the fluid absorbing modules are packed in an appropriate bag, or are wrapped in toilet paper and then placed in a garbage bin. Also, special small garbage bins have been developed in which used tampons can be collected.

However, removing a tampon from the vagina is usually unpleasant and unhygienic, especially with heavy menstruation. Used tampons can also spread a penetrating smell.

The object of the invention is to obtain an assembly for taking up menstrual fluid according to the opening paragraph with which, while maintaining the advantages, at least one of the disadvantages is counteracted. In particular, the object of the invention is to obtain an assembly for taking up menstrual fluid according to the opening paragraph which can be removed in a more hygienic manner. To that end, the cord comprises a string and a covering with an open and closed end which, before use of the assembly, substantially surrounds the string, and wherein the closed end of the covering is fixed to the string adjacent the first end of the cord.

Through the use of a string with covering, the fluid absorbing module can be pulled into the covering without the fingers coming into contact with the module. Thus, the fluid absorbing module can be hygienically removed from the vagina. Furthermore, the module can be wrapped in the covering before placing it in a garbage bin or the like. Spreading of odor is thus prevented.

More specifically, removal and handling of the fluid absorbing module can take place by engaging the free end of the string with a first hand, and, with a second hand, reaching into the covering as far as the closed end of the covering which is fixed to the string adjacent the first end of the cord. By thereupon pulling the free end of the string with the first hand, the module is pulled into the covering, while the second hand folds the covering over the fluid absorbing module. Then, the open end of the covering can be wrapped around the fluid absorbing module so that the module is completely received in the covering.

As the covering, before use of the assembly, substantially surrounds the string, preferably via a detachable attachment, irritation when using a fluid absorbing module designed as a tampon is limited. Before removing the tampon from the vagina, the covering can then be released from the string, ready for receiving the tampon.

The invention further relates to a method for processing an assembly.

Further advantageous embodiments of the invention are represented in the subclaims.

The invention will be further elucidated on the basis of exemplary embodiments which are represented in the drawing. In the drawing.

The Figures are only a schematic representation of the preferred embodiment of the invention. In the Figures, identical or corresponding parts are indicated with the same reference numerals.

Figure 1:
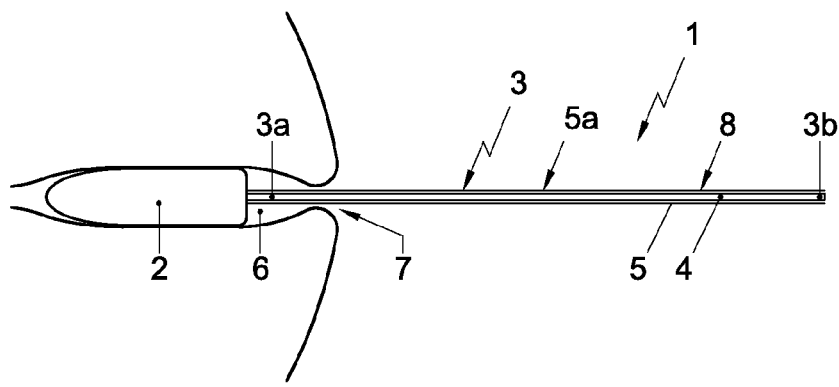
FIG. 1 shows a schematic view of an assembly according to the invention.

FIG. 1 shows a schematic view of an assembly 1 according to the invention. The assembly 1 comprises a fluid absorbing module designed as a tampon 2 and a cord 3 connected thereto. The tampon 2 has been introduced via the introitus 7 into the vagina 6. The cord 3 has a first end 3a and a second end 3b. The first end 3a is connected to the tampon 2, while the second end 3b is free. The cord 3 comprises a string 4 having a covering 5, also called bag, around it. Preferably, the string 4 is a cotton string. However, the string can also be manufactured from another natural material, such as hemp, or from a synthetic material, such as nylon. Before use of the tampon 2, the bag 5 is attached tightly around the string 4 so that the covering substantially surrounds the string. The bag 5 is substantially cylindrical or conical. The bag further has a closed end and an open end. The closed end is fixed adjacent the first end 3a of the cord 3 to the string 4, so that the string 4 is located within sidewalls of the bag. Preferably, the closed end of the covering is fixed to the string in a fluid-tight manner, so that leakage from the covering is prevented.

The bag 5 can surround the string in different manners, for instance in a folded condition, like a concertina, or wound around the string in a spiral shape. Also, the bag can surround the string in a manner differently folded, wound, crumpled, turned and/or otherwise. Preferably, the bag 5 is durably detachably attached to the string, for instance via a glue connection or by pressing the bag around the string 4. However, the attachment of the bag to the string can simply be eliminated by the user, for instance by applying a frictional force to the cord 3.

The bag 5 is preferably non-transparent. By designing the bag to be opaque, the content of the bag can be hidden from view so that some privacy is involved after disposal of the bag. Although it is not preferred, instead of opaque, the bag 5 can in principle be designed to be translucent or even transparent. Further, the bag is preferably manufactured from a substantially non fluid-transmissive material or foil, for instance a plastic, more particularly a polymer, still more particularly a nylon. Using fluid-proof material prevents leakage.

Preferably, the outside of the cord 3, and therefore a side 5a of the bag 5 initially located at the outside, has a soft feel to prevent skin irritation. Preferably, further, the side 5a of the bag 5 initially located at the outside, which at a later stage, as described in the following, forms the side 5a' located at the inside of the bag, is not smooth so as to prevent and/or absorb a fluid flow of the taken-up fluid such as blood, urine and the like, in the absorbing module, in particular during removal of the tampon from the vagina. To that end, the covering, at the side 5a which before use of the assembly faces away from the string, is provided with a layer 8 with skin-friendly and/or fluid flow reducing material, for instance a coating of polyurethane (PU) or spray-cotton.

In an advantageous manner, the string 4 has a greater length than the length of the tampon 2, so that the bag after reception of the tampon 2 can be tied up with the string 4. However, in principle, the string can also be shorter. Closing the bag off can then take place in another way, for instance by tying a knot in the bag.

Further, the dimensions of the covering are preferably selected such that, after taking up fluid, the fluid absorbing module is completely receivable in the covering 5.

The fluid absorbing module 2 is preferably formed as a cylindrical body, so that the module can be received in the vagina in a somewhat form locking manner.

Most preferably, the open end of the covering in folded out condition forms an opening with dimensions which amply exceed the maximum dimensions of the fluid absorbing module 2 in a cross section. As a result, the tampon can easily be pulled into the bag 5, because the volume of the covering is suited thereto.

Figure 2A:
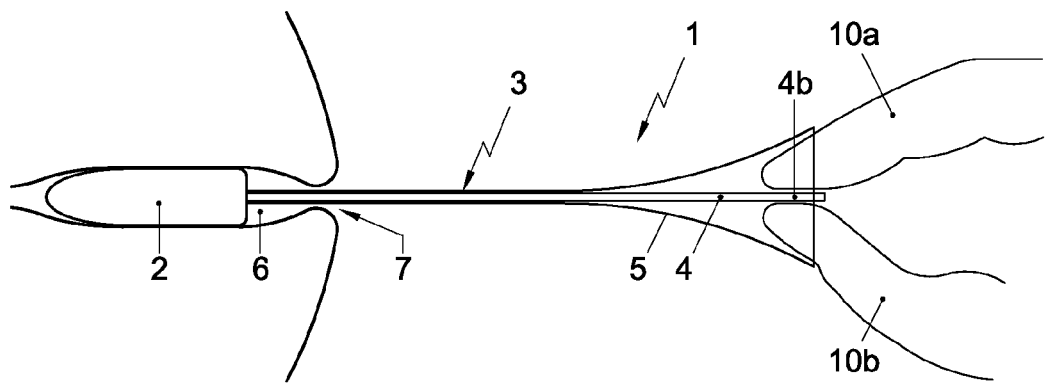
FIG. 2A shows a schematic view of the assembly as shown in FIG. 1 in a first position.
Figure 2B:
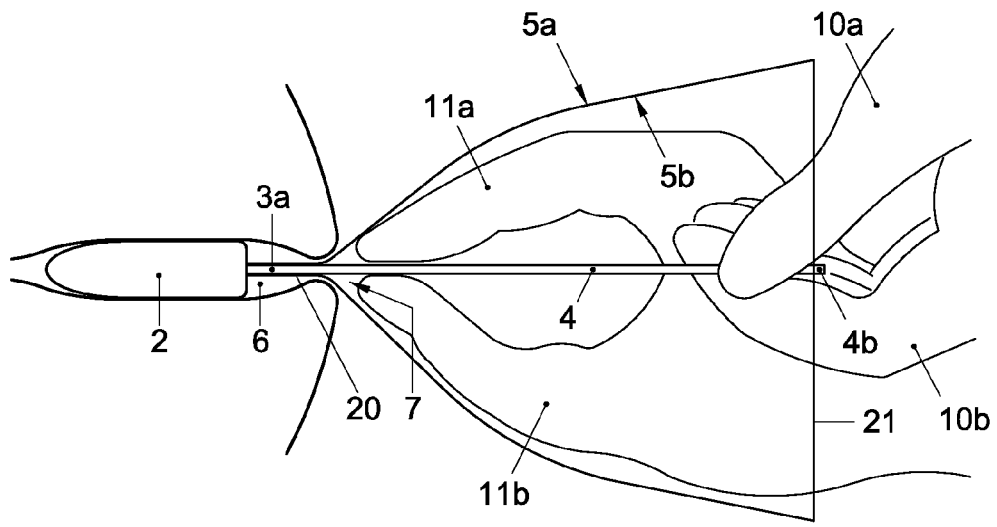
FIG. 2B shows a schematic view of the assembly as shown in FIG. 1 in a second position.
Figure 2C:
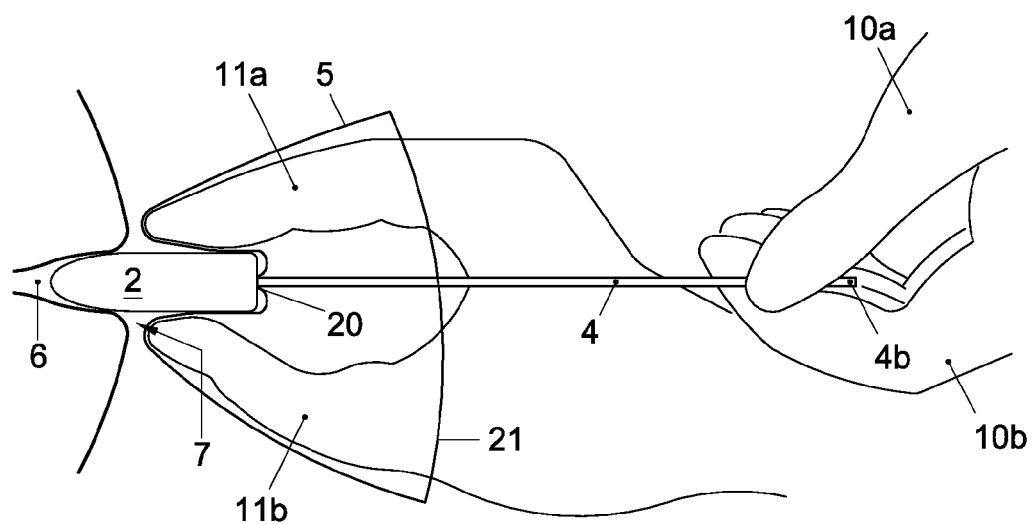
FIG. 2C shows a schematic view of the assembly as shown in FIG. 1 in a third position.
Figure 3:
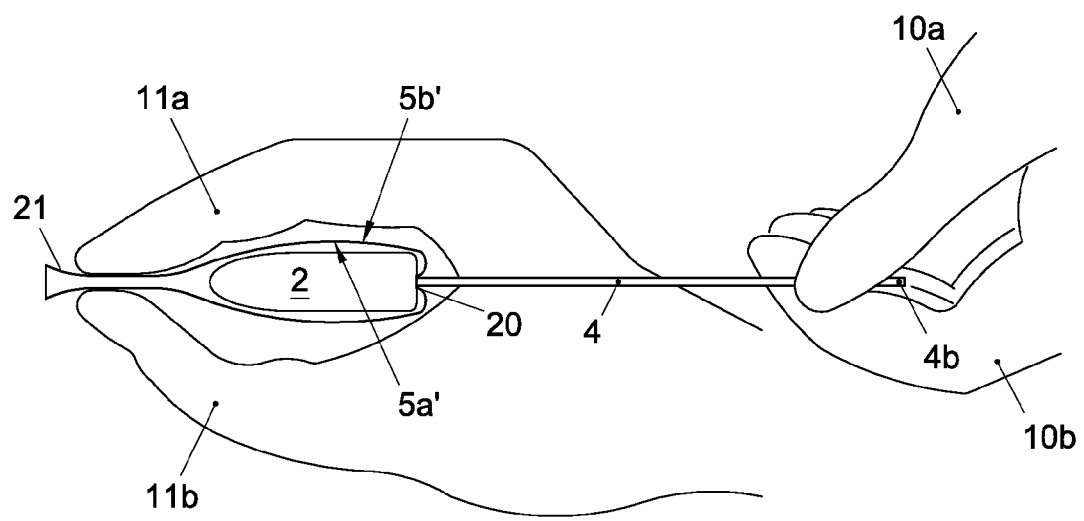
FIG. 3 shows a schematic view of the assembly as shown in FIG. 1 in a fourth position.

FIGS. 2A-C show a schematic view of the assembly as shown in FIG. 1 in a first, second and third position, respectively. Further, FIG. 3 shows the assembly in a fourth position.

In the first position, it is shown that the covering 5 is disengaged from the string 4, except for the closed end 20, before engaging the free end 4b of the string 4. Thereupon, the free end 4b of a string 4 is actually engaged by fingers 10a, b of a first hand.

In the second position, it is shown that fingers 11a,b of a second hand reach into the bag 5, via the open end 21, as far as the closed end 20 of the bag 5 which is fixed to the string 4 adjacent the first end 3a of the cord 3.

In the third position it is shown that the fingers 10a, b of the first hand pull the free end 4b of the string while fingers 11a, b of the second hand fold the bag around the tampon 2. The bag 5 is thereby turned back. Owing to this turning back, the initially outer part 5a of the bag then forms the inner side 5a' of the bag. In the same manner, the initially inner part 5b of the bag, which is clean and hygienic, forms the outer part of the bag 5b' after turning back. In order to facilitate the folding process, fingers 11a, b of the second hand, while the free end 4b of the string is being pulled, can be located in circumferential direction around the taken-up part of the tampon 2. Here, the fingers 11a, b can be placed around the introitus 7. The risk of fluid leaking is thereby minimized. In principle, however, it is also possible to place the fingers 11a, b somewhat before the introitus 7.

In the fourth position, it is shown that the bag is also folded back adjacent the open end 21, around the tampon, so that the bag can be wholly closed off after the tampon has been pulled into the bag.

By following the above-described procedure, contact of the fingers with the tampon 2 is avoided, so that a hygienic removal of the tampon is enabled.

It is noted that the above-described operations performed by the second hand in fact take place with the aid of a limited number of fingers 11 of the second hand, preferably only two fingers, for instance the thumb and the index finger, or the index finger and the middle finger. This results in more room to manoeuvre in the covering and an ergonomically more attractive process is obtained. Naturally, as an alternative, other fingers too, or even all fingers of the second hand can be involved in the described operations.

In a comparable manner, engaging the string end 4b with the first hand can be carried out in different manners, for instance with the aid of thumb and index finger 10, see for instance FIG. 2B. Another possibility is engaging with three fingers, for instance the thumb, index finger and middle finger.

It is further noted that in accordance with an aspect of the invention, only the cord is designed differently, albeit radically, from the known assembly. As a result, the manufacture of an assembly can be adapted relatively simply to arrive at the assembly according to the invention. Thus, only the cord needs to be adapted.

The invention is not limited to the exemplary embodiments described here. Many variants are possible.

The assembly according to the invention can be suited not only for taking up menstrual fluid, but also for taking up other fluid. For instance, an assembly of a teabag with a cord connected thereto can also be used according to the invention.

Such variants will be clear to the skilled person and are understood to be within the scope of the invention, as set forth in the following claims.

The invention claimed is:

1. An assembly for taking up menstrual fluid, comprising; a fluid absorbing module; and
a cord having a first end and a second end, the first end of the cord is connected to the fluid absorbing module and the second end of the cord is free, wherein the cord comprises a string and a covering with an open end and a closed end, wherein before use of the assembly, the covering substantially surrounds the string, and wherein the closed end of the covering is fixed to the string adjacent the first end of the cord, wherein a part of the covering is detachably attached to the string.

2. The assembly according to claim 1, wherein the closed end of the covering is fixed to the string in a fluid-tight manner.

3. The assembly according to claim 1, wherein the covering is non-transparent.

4. The assembly according to claim 1, wherein the covering is manufactured from a non fluid-transmissive material.

5. The assembly according to claim 1, wherein a side of the covering, which before use of the assembly faces away from the string, is provided with a layer of skin-friendly material.

6. The assembly according to claim 1, wherein the string has a greater length than a length of the fluid absorbing module.

7. The assembly according to claim 1, wherein dimensions of the covering are selected such that after fluid take-up, the fluid absorbing module is completely receivable in the covering.

8. The assembly according to claim 1, wherein the fluid absorbing module comprises a substantially cylindrical body.

9. The assembly according to claim 1, wherein the open end of the covering in a folded open position forms an opening with dimensions which amply exceed maximum dimensions of the fluid absorbing module in a cross section.

10. The assembly according to claim 1, wherein the assembly forms a tampon.

11. An assembly for taking up menstrual fluid, comprising; a fluid absorbing module; and
a cord having a first end and a second end, the first end of the cord is connected to the fluid absorbing module and the second end of the cord is free, wherein the cord comprises a string and a covering with an open end and a closed end, wherein before use of the assembly, the covering substantially surrounds the string, and wherein the closed end of the covering is fixed to the string adjacent the first end of the cord, wherein a part of the covering is wound around the string.

12. An assembly for taking up menstrual fluid, comprising;
a fluid absorbing module; and
a cord having a first end and a second end, the first end of the cord is connected to the fluid absorbing module and the second end of the cord is free, wherein the cord comprises a string and a covering with an open end and a closed end, wherein before use of the assembly, the covering substantially surrounds the string, and wherein the closed end of the covering is connected to the fluid absorbing module, wherein a side of the covering, which before use of the assembly faces away from the string, is slightly fluid absorbent.

13. A method for processing an assembly for taking up menstrual fluid, comprising a fluid absorbing module and a cord of which a first end is connected to the fluid absorbing module and of which a second end is free, the method comprising the steps of:
engaging a free end of a string which forms part of the cord with a first hand, while a covering having a closed end fixed to the string adjacent the first end of the cord, and which also forms part of the cord, substantially surrounds the string before use of the assembly, wherein the covering is attached tightly around the string;
reaching into a covering of the cord with a second hand as far as a closed end of the covering which is fixed to the string adjacent the first end of the cord;
pulling the free end of the string with the first hand while the second hand folds the covering around the fluid absorbing module; and
folding the covering back adjacent an open end thereof, around the fluid absorbing module.

14. The method according to claim 13, including locating the ends of fingers of the second hand in a circumferential direction around a taken-up part of the fluid absorbing module, while the free end of the string is being pulled.

15. The method according to claim 13, including placing the ends of fingers of the second hand around an introitus, while the free end of the string is being pulled.

16. The method according to claim 13, including closing the covering off around the fluid absorbing module.

17. The method according to claim 13, including freeing the string from the covering, except for the closed end, before engaging the free end of the string.

18. An assembly for taking up menstrual fluid, comprising;
a fluid absorbing module; and
a cord having a first end and a second end, the first end of the cord is connected to the fluid absorbing module and the second end of the cord is free, wherein the cord comprises a string and a covering with an open end and a closed end, wherein before use of the assembly, the covering substantially surrounds the string, and wherein the closed end of the covering is fixed to the string adjacent the first end of the cord, wherein the covering is attached tightly around the string.

* * * * *